United States Patent [19]

Ager et al.

[11] 3,965,219

[45] June 22, 1976

[54] CONTINUOUS PROCESS FOR THE ESTERIFICATION OF PHOSPHONITRILIC CHLORIDE POLYMERS

[75] Inventors: John W. Ager, Princeton, N.J.; Thomas M. Fekete, Yardley, Pa.

[73] Assignee: FMC Corporation, Philadelphia, Pa.

[22] Filed: Dec. 18, 1974

[21] Appl. No.: 533,874

[52] U.S. Cl. ............................. 260/973; 260/927 N
[51] Int. Cl.² ........................................ C07F 9/00
[58] Field of Search ....................... 260/927 N, 973

[56] References Cited
UNITED STATES PATENTS

| | | | |
|---|---|---|---|
| 2,192,921 | 3/1940 | Lipkin | 260/927 N |
| 2,586,312 | 2/1952 | Dishon et al. | 260/927 N X |
| 3,869,294 | 4/1975 | Lanier et al. | 260/927 N X |

*Primary Examiner*—Anton H. Sutto

[57] ABSTRACT

Phosphonitrilic chloride polymers are continuously esterified in a process wherein a solution of phosphonitrilic chloride polymer in an organic solvent is concurrently fed into a reactor with an alkanol solution of an alkali metal alkoxide, and the product phosphonitrilic chloride ester is continuously withdrawn and separated.

7 Claims, No Drawings

CONTINUOUS PROCESS FOR THE ESTERIFICATION OF PHOSPHONITRILIC CHLORIDE POLYMERS

This invention relates to alkoxy esters of polymeric phosphonitrilic chlorides. More particularly, this invention relates to a novel continuous process for producing phosphonitrilic chloride polymers esterified with alkoxy groups having 1 to 12 carbon atoms.

Phosphonitrilic chloride esters, more specifically the alkoxylated phosphazenes, are known and are described, for example, in U.S. Pat. No. 3,794,701, issued Feb. 26, 1974 to Bik, wherein hexachlorophosphazene is reacted with a monovalent alkanol and pyridine; U.S. Pat. No. 3,455,713, issued July 15, 1969; U.S. Pat. No. 3,505,087 issued Apr. 7, 1970 and U.S. Pat. No. 3,532,526, issued Oct. 6, 1970 to Godfrey; U.S. Pat. No. 2,192,921, issued Mar. 12, 1940 to Lipkin, wherein the reaction of phosphonitrilic chlorides generally with metallic salts of organic compounds is disclosed and U.S. Pat. No. 2,586,312, issued Feb. 19, 1952 to Dishon et al, wherein esterification of rubbery phosphonitrilic chloride polymers with alcohols is disclosed; and West German Application 1,906,387 published Sept. 3, 1970 describing partial esters made in the presence of pyridine. These representative prior art processes have a number of disadvantages, especially with regard to the requirement of relatively long reaction times or the use of acid-binding agents, such as pyridine, which require additional processing and regeneration steps. It is an object of the present invention to provide for an efficient, continuous process for the esterification of phosphonitrilic chloride polymers.

In accordance with the present invention, there is provided a novel continuous process for the esterification of phosphonitrilic chloride polymers comprising reacting (a) a phosphonitrilic chloride polymer of the general formula $-(NPCl_2)-n$, where $n$ is at least 3, with (b) an alkali metal alkoxide having 1 to 12, preferably 2 to 6 carbon atoms, by feeding said reactants to a reaction zone containing a circulating reaction mixture maintained at a temperature of about 50° to 150°C comprising the reaction product phosphonitrilic chloride ester, dissolved in an inert organic solvent therefor, while continuously withdrawing a portion of said reaction mixture from the reaction zone.

The phosphonitrilic chloride employed in the process of the present invention is a polymer represented by the formula $-(NPCl_2)-n$ where $n$ is an integer of at least 3, the average value being up to about 9 for cyclic polymers and 15 to 20 or more for linear polymers. Both linear and cyclic polymers and mixtures of same may be employed. Preferably, there is used a predominantly cyclic phosphonitrilic chloride polymer, such as a polymer in which about 50% by weight or more are cyclic, trimeric to heptameric oligomers, most preferably 75 to 95% by weight of trimeric to heptameric cyclic oligomers, with 50 to 60% of the cyclic oligomers being trimers and 20 to 30% being tetramers. The polymeric phosphonitrilic chloride is preferably added in diluted state such as a solution in an inert organic solvent. Suitable solvents include the halogenated aromatic and aliphatic hydrocarbon solvents such as tetrachloroethane, chloroform, carbon tetrachloride, chlorobenzene, o- or m- dichlorobenzene or trichlorobenzene. In the preferred embodiments, in which an alkanol such as propanol is present, it is preferred to use a solvent from which the alkanol is easily separated by distillation; to this end it is preferred to use a solvent which does not azeotrope with the alkanol and has a considerably higher boiling point than the alkanol, such as a chlorinated aromatic hydrocarbon. Monochlorobenzene and o-dichlorobenzene are particularly suitable. Alkanes such as heptane, octane, isooctane, while less preferable, are also suitable.

The concentration of phosphonitrilic chloride polymer in the feed solution may, for instance, be between about 15 to 30% by weight and preferably a 20 to 25% by weight solution is employed.

The alkali metal alkoxide is preferably added in diluted state, most preferably a solution thereof in an alkanol. The alkali metal alkoxides and alkanols may generally be described as those having from 1 to 12 carbon atoms, preferably 2 to 6 carbon atoms. Alkoxides of alkali metals generally are suitable, with potassium and sodium being particularly suitable. Sodium alkoxides are preferred for economic reasons. Exemplary alkoxides are sodium methoxide, sodium ethoxide, sodium propoxide, sodium butoxide, and the like. Mixtures of alkoxides may be used and it is within the scope of the present invention to employ mixed alkanol solvents containing a particular alkoxide, or with a mixture of different metal alkoxides, if it is desired to prepare esters containing a mixture of alkoxy groups. Thus, for example, a mixture of propanol and ethanol can be used as a solvent with an alkoxide such as sodium propoxide. Particularly preferred are solutions of sodium propoxide in n-propanol.

The concentration of the alkoxide-alkanol solution is somewhat variable depending on the particular solubility of the alkoxide being used. Generally, an alkoxide concentration of about 15 to 30% by weight is employed. For sodium propoxide in n-propanol, preferably a concentration of 15 to 25% by weight, most preferably 18 to 20% is used.

In carrying out the process of the present invention, the phosphonitrilic chloride solution and the alkoxide solution are preferably simultaneously metered into a stirred reactor and the reaction mixture is continuously circulated while maintained at a temperature of between about 50° to 150°C, and preferably from about 90° to 125°C. Generally, the reaction is effected under reflux and the reaction temperature is the reflux temperature of the solvent system at the particular pressure prevailing in the reactor, which may be atmospheric, subatmospheric or superatmospheric pressure. When the preferred solvent system is employed, that is, o-dichlorobenzene and propanol, a temperature of 100° to 110°C may be maintained at atmospheric pressure when the propanol (which refluxes) is the major solvent or diluent constituent. When the propanol is present in minor proportions, e.g., 5–30%, such as 10%, subatmospheric pressures may be used to provide a reflux of propanol at those temperatures.

The relative proportions of alkoxide and phosphonitrilic chloride polymer are governed generally by stoichiometric considerations. Generally, for an equivalent unit of phosphonitrilic chloride polymer, that is, a $-(NPCl_2)-n$ unit, 2 mols of propoxide are necessary to effect full esterification by replacement of both chlorines attached to the phosphorus. Any alkanol which reacts with phosphonitrilic chloride will be regenerated, since the HCl by-product of this reaction will react with alkoxide to produce alkanol. Thus, the stoichiometry may be based solely on the quantity of alkoxide used.

Generally, there are introduced into the reactor from about 1.0 to 2.5 mols of alkoxide per equivalent unit of phosphonitrilic chloride polymer, that is, per $(PNCl_2)$ unit. The process of the present invention is characterized by excellent utilization of metal alkoxide with conversions of metal alkoxide such as sodium propoxide being on the order of 90 to 95% and higher. The precise ratio of alkoxide to $(PNCl_2)$ will be dependent on the desired chlorine content of the ester product. The preferred ratio of mols of alkoxide per $(PNCl_2)$ equivalent unit is from about 1.2 to 1.8.

The average residence time of the reactants in the reaction zone may vary generally between about 10 and 100 minutes, preferably an average residence time of about 30 to 60 minutes is employed.

It is desirable for many purposes, such as when phosphonitrilic chloride esters are employed as flame-retardant additives for regenerated cellulose such as is disclosed in Belgian Patent 810,316 (1974), to have the finished ester contain a minor proportion of unreacted chlorine, generally between about 3 to 20% or 30% by weight. The process of the present invention is advantageous in that the chlorine content is readily controllable by adjusting the feed ratios, for example, by adjusting the concentration of the propoxide-propanol feed solution. A decrease in the mol ratio of alkoxide to phosphonitrilic chloride polymer tends to increase the quantity of unreacted chlorine in the ester product.

After the initial start-up and line-out periods, the continuous reaction may be carried out under substantially steady state conditions. Thus, there may be employed substantially constant continuous feed rates and substantially constant withdrawal rates such as continuously withdrawing the reaction product at a rate equivalent to the feed rate. It will be understood that the product withdrawn from the circulating reaction mixture in the reaction zone will have substantially the same composition as said circulating mixture. The concentration of reactants in that mixture will generally be relatively low, and only a fraction usually less than 20%, of the concentration in the feed. For instance, the concentration of the reactants in the reaction mixture may be well below 2%, such as below 1%. Thus, in Example I (below) the feed solution of phosphonitrilic chloride polymers contains about 20% of the latter and said polymers constitute about 7% of the total feed, but in the circulating reaction mixture (into which the feed solutions are introduced) the concentration of the feed polymers is below 1%, as can be calculated from the fact that the product is obtained in about 90% yield.

Also suitable, but less preferable, is the utilization of a pre-mixing technique whereby the alkoxide and phosphonitrilic chloride feeds may be pre-mixed at lower temperatures, for example, 15° to 20°C, and the mixed feeds may then be introduced into the circulating reaction mixture.

The reaction mixture removed from the stirred reactor may be purified (and the reaction terminated) by treating it with water or with a dilute aqueous acidic solution, such as an HCl solution, followed by phase separation. Any unreacted alkoxide will be converted to NaOH and NaCl (depending on the acidity of the wash solution) and alkanol. It is generally preferable to employ a dilute 1 to 10% by weight aqueous HCl solution, since some products tend to emulsify and thereby delay phase separation. The wash may be effected with agitation at room temperature with from about 25 to 75% by volume water or dilute HCl solution in a mixing zone. The washed effluent may then be withdrawn from the mixing zone and allowed to separate into an aqueous layer and an organic layer containing the desired product. The product may be isolated by stripping solvent from the organic layer preferably under vacuum so that the temperature of the mixture is maintained below about 125°C, for example, with a vacuum of about 30 mm. Hg and a temperature of about 100°C. The stripped organic solvent may be recycled to the process by being used to provide phosphonitrilic chloride reactant solution.

In one aspect, the reaction is effected while continuously distilling the alkanol solvent from the reaction mixture in the reaction vessel while retaining the inert organic solvent therein. In this case, the solvent in the ester product mixture withdrawn from the reactor vessel is predominantly inert organic solvent. This solution may then be washed and allowed to separate as described above, and the organic layer may be solvent stripped under vacuum to recover the product phosphonitrilic chloride ester. Alkanol, such as propanol, may be distilled out of the reaction mixture by fitting the reactor with a fractional distillation column and collecting an alkanol overhead. When propanol is employed, it is advantageous to use subatmospheric pressure, for example, about 510 mm. Hg, and to maintain a reaction vessel temperature of about 100°–108°C. This later technique is advantageous in that it provides a supply of purified alkanol which can be recycled to the process by being used in preparing the alkoxide-alkanol reactant solution. This solution is prepared by simply dissolving alkali metal, such as sodium, in an alkanol in appropriate quantities.

The final products are generally liquid alkoxy phosphazenes having an unreacted chlorine content of about 5 to 30% by weight. The preferred products, propoxy phosphazenes, have an average molecular weight of about 600–900.

The invention is further illustrated by the following examples which should not be considered as limitative of its scope.

EXAMPLE I

A 20% by weight solution of phosphonitrilic chloride polymers in dichlorobenzene was prepared. The polymers were 95% cyclic and the cyclic portion contained about 55% trimers, 25% tetramers and about 20% pentamers, hexamers and heptamers. A 19% by weight solution of sodium propoxide was prepared by dissolving sodium in n-propanol. The two solutions were simultaneously fed to a glass reaction vessel equipped with a condenser and maintained at atmospheric pressure. During the start-up period (about 40 minutes) all the feed was retained and thereafter (by continuous withdrawal of overflow reaction mixture) the liquid level of the reactor was maintained at a capacity of 1350 ml. During the run, the reaction mixture was continuously circulated in the vessel and maintained at a reflux temperature of 103°C. The continuously withdrawn reaction mixture was fed into a 500 ml washing flask where wash water (90 ml conc. HCl +3 liters $H_2O$) was continuously added at such rate so as to maintain the pH of the wash vessel effluent at 6. This effluent was composed of both aqueous and organic phases. At a constant rate over a period of 150 minutes there were added to the reaction vessel 1,675 ml of phosphonitrilic chloride solution and 3,220 ml of sodium propoxide solution. After 150 minutes of continuous operation, the contents of the reaction vessel were cooled to about 25°C mixed with acidic wash solution and added to the washed effluent previously obtained. Average residence time in the reaction vessel was 40 minutes. There was obtained 4,661 grams of an organic layer and 2,502 grams of a water layer. The organic layer was solvent stripped at 30 mm. Hg and 100°C and there was obtained 600 grams (90% yield based on $PNCl_2$ feed) of a liquid ester product which had an acid number of 30 and a chlorine content of 5% by weight.

EXAMPLE II

The 20% solution of phosphonitrilic chloride polymers of Example I was fed to a cooled mixing vessel at a rate of 10.5 ml/min. There was concurrently fed to this vessel an 18.5% by weight solution of sodium propoxide in n-propanol at a rate of 24 ml/min. The reactants reacted partially and exothermically, in the mixing vessel which was cooled to 15°–20°C. The mixture was continuously withdrawn from the mixing vessel (the residence time therein being 8 minutes) and fed directly to an esterifier vessel where reaction continued at a temperature of 103°C under propanol reflux at atmospheric pressure. Average residence time in the esterifier vessel was maintained at 40 minutes by continuous withdrawal of reaction mixture after the initial start-up period. The esterifier effluent was continuously withdrawn and washed at room temperature with a solution of 800 ml water, 200 ml propanol and 13 ml hydrochloric acid at a rate of 50 ml/min. The washed effluent (pH 1.5) separated quickly into a clear water phase and a slightly cloudy organic phase. The organic phase was solvent stripped as in Example I to obtain a liquid ester product having an acid number of 29 and a chlorine content of 6% by weight.

EXAMPLE III

A 20% solution of phosphonitrilic chloride polymer (81% cyclic, 19% linear mixed trimeric to heptameric liquid oligomers) in dichlorobenzene was metered into a reaction vessel at the rate of 11 ml/min. A 19% by weight solution of sodium propoxide and propanol was simultaneously added to the same vessel at a flow rate of 25 ml/min. The reaction mixture was maintained at reflux temperature of 103°C at atmospheric pressure. After the start-up period, the reaction mixture was continuously withdrawn to a washing vessel where a wash solution (800 ml $H_2O$, 200 ml propanol, 13 ml hydrochloric acid) was introduced at a rate of 13 ml/min. The pH of the wash effluent was 7 ±0.5. Average residence time in the reaction vessel was 40 minutes. The organic layer was solvent stripped to obtain an ester product having an acid number of 14 and a chlorine content of 10% by weight.

EXAMPLE IV

Example III was repeated except that the wash solution used was 1 liter of water plus 13 ml hydrochloric acid. No propanol was used in the wash solution. The ester product obtained had an acid number of 8 and a chlorine content of 7.8%.

EXAMPLE V

Continuous esterification was carried out as described in the preceding example, except that the reaction vessel was fitted with a distillation column for continuous removal of propanol by vacuum distillation with partial reflux under vacuum. The solutions used and the concentrations thereof were the same as in Example I. The initial charge in the esterifier flask was 255 grams of phosphonitrilic chloride solution and 45 grams of sodium propoxide solution. Phosphonitrilic chloride solution was introduced at a feed rate of 10 ml/min.; propoxide solution feed rate was 25 ml/min. The reaction vessel was maintained at a temperature of 106° to 108°C and a pressure of about 510 mm. Hg absolute. Propanol was continuously removed overhead; as a result, the weight ratio of propanol to dichlorobenzene in the reaction mixture was maintained at about 15:85 to 12:88. In 6 hours of operation, 4,950 grams of phosphonitrilic chloride solution was used and 6,300 grams of material was collected overhead. Average residence time in the reaction vessel was 80–90 minutes. The overhead distillate contained about 2% by weight dichlorobenzene in the propanol. After the start-up period which continued until 1000 ml of liquid accumulated in the reactor, a bottom draw metering pump was used to withdraw reaction mixture continuously from the base of the reactor and it was regulated to maintain 1000 ml of liquid in the reactor. The withdrawn product was washed in batches with twice its volume of water. The pH of the wash was about 11. 1,390 grams of ester product (100% yield) was obtained having an acid number of 0 and a chlorine content of 7.3%.

EXAMPLE VI

Example II was repeated except that the alkanol solvent was a mixture of equal volumes of propanol and ethanol. A product having an acid number of 6.6 and a chlorine content of 9% was obtained.

What is claimed is:

1. A continuous process for the esterification of phosphonitrilic chloride polymers comprising reacting (a) a phosphonitrilic chloride polymer of the general formula $(NPCl_2)n$, where n is at least 3, in an inert organic solvent with (b) an alkali metal alkoxide having 1 to 12 carbon atoms in an alkanol solvent, by continuously feeding said reactants to a reaction zone maintained at a temperature of 90 to 125 °C containing a circulating reaction mixture comprising phosphonitrilic ester reaction products and, while adding the reactants, continuously withdrawing said reaction mixture from said reaction zone such that the average residence time of the reactants in said reaction zone is between about 10 and 100 minutes.

2. The process of claim 1 wherein said phosphonitrilic chloride polymer contains a major amount of cyclic polymers.

3. The process of claim 2 wherein the phosphonitrilic chloride polymer contains 75 to 95% by weight of cyclic trimeric to heptameric oligomers with 50 to 60% of the cyclic oligomers being trimers and 20 to 30% being tetramers.

4. The process of claim 1 wherein said alkanol is propanol and said alkali metal alkoxide is sodium propoxide.

5. The process of claim 1 wherein said inert organic solvent is o- or m-dichlorobenzene.

6. The process of claim 1 wherein the withdrawn reaction mixture is continuously washed with water or an aqueous acidic solution, the organic and aqueous layers are allowed to separate and product phosphonitrilic chloride ester is isolated by removing solvent from the organic layer.

7. The process of claim 1 wherein alkanol is removed during the course of the reaction by distillation from the reaction mixture.

* * * * *